United States Patent [19] [11] 4,127,733
Nelson [45] Nov. 28, 1978

[54] 2-DECARBOXY-2-HYDROXYMETHYL-17-PHENYL-11-DEOXY-PGF₁ ANALOGS

[75] Inventor: Norman A. Nelson, Galesburg, Mich.

[73] Assignee: The Upjohn Company, Kalamazoo, Mich.

[21] Appl. No.: 822,036

[22] Filed: Aug. 5, 1977

Related U.S. Application Data

[62] Division of Ser. No. 647,357, Jan. 8, 1976, Pat. No. 4,055,602.

[51] Int. Cl.² ............................................. C07C 177/00
[52] U.S. Cl. ................................... 568/807; 568/645; 568/646; 424/341; 424/343
[58] Field of Search .......... 260/618 R, 618 D, 611 A; 568/807

[56] References Cited

U.S. PATENT DOCUMENTS

| | | | |
|---|---|---|---|
| 3,914,282 | 10/1975 | Pike | 560/121 |
| 3,932,463 | 1/1976 | Schaub et al. | 560/121 |
| 3,933,889 | 1/1976 | Magerlein | 560/121 |
| 3,959,346 | 5/1976 | Schneidner | 560/121 |
| 3,962,293 | 6/1976 | Magerlein | 560/121 |

OTHER PUBLICATIONS

Burger, "Medicinal Chemistry" pp. 81–82 (1960).
Derwent Farmdoc CPI No. 07432w/05 (11-07-73).
Derwent Farmdoc CPI No. 13108w/08 (02-08-73).

*Primary Examiner*—Gerald A. Schwartz
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

59 Claims, No Drawings

2-DECARBOXY-2-HYDROXYMETHYL-17-PHENYL-11-DEOXY-PGF₁ ANALOGS

The present application is a divisional application of Ser. No. 647,357, filed Jan. 8, 1976, now issued as U.S. Pat. No. 4,055,602.

The present invention relates to prostaglandin analogs, for which the essential material constituting disclosure therefor is incorporated by reference here from U.S. Pat. No. 4,055,602, issued Oct. 25, 1977.

I claim:

1. A prostaglandin analog of the formula

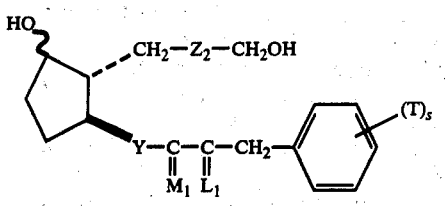

wherein Y is trans—CH=CH—;
wherein $M_1$ is

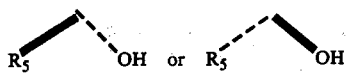

wherein $R_5$ is hydrogen or methyl;
wherein $L_1$ is

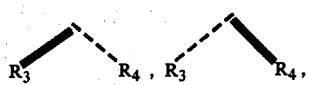

or a mixture of

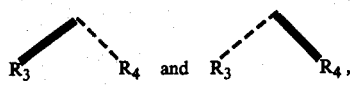

wherein $R_3$ and $R_4$ are hydrogen, methyl, or fluoro, being the same or different, with the proviso that one of $R_3$ and $R_4$ is methyl only when the other is hydrogen or methyl;
wherein $Z_2$ is
cis—CH=CH—CH$_2$—(CH$_2$)$_g$—CF$_2$—;
cis—CH$_2$—CH=CH—(CH$_2$)$_g$—CH$_2$—; or
—(CH$_2$)$_3$—(CH$_2$)$_g$—CF$_2$—;
wherein $g$ is one, 2, or 3; and
wherein $s$ is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl.

2. A compound according to claim 1, wherein s is zero or one and T is chloro, fluoro, or trifluoromethyl.

3. A compound according to claim 2, wherein $Z_2$ is cis—CH=CH—CH$_2$—(CH$_2$)$_g$—CF$_2$—.

4. A compound according to claim 3, wherein g is one.

5. A compound according to claim 4, wherein at least one of $R_3$ and $R_4$ is fluoro.

6. A compound according to claim 5, wherein $R_3$ and $R_4$ are both fluoro.

7. A compound according to claim 6, wherein $R_5$ is methyl.

8. 2-Decarboxy-2-hydroxymethyl-2,2,16,16-tetrafluoro-15-methyl-17-phenyl-18,19,20-trinor-11-deoxy-PGF$_2$α, a compound according to claim 7.

9. A compound according to claim 6, wherein $R_5$ is hydrogen.

10. 2-Decarboxy-2-hydroxymethyl-2,2,16,16-tetrafluoro-17-phenyl-18,19,20-trinor-11-deoxy-PGF$_2$α, a compound according to claim 9.

11. A compound according to claim 4, wherein at least one of $R_3$ and $R_4$ is methyl.

12. A compound according to claim 11, wherein $R_3$ and $R_4$ are both methyl.

13. A compound according to claim 12, wherein $R_5$ is methyl.

14. 2-Decarboxy-2-hydroxymethyl-2,2-difluoro-15,16,16-trimethyl-17-phenyl-18,19,20-trinor-11-deoxy-PGF$_2$α, a compound according to claim 13.

15. A compound according to claim 12, wherein $R_5$ is hydrogen.

16. 2-Decarboxy-2-hydroxymethyl-2,2-difluoro-16,16-dimethyl-17-phenyl-18,19,20-trinor-11-deoxy-PGF$_2$α, a compound according to claim 15.

17. A compound according to claim 4, wherein $R_3$ and $R_4$ are both hydrogen.

18. A compound according to claim 17, wherein $R_5$ is hydrogen.

19. 2-Decarboxy-2-hydroxymethyl-2,2-difluoro-15-methyl-17-phenyl-18,19,20-trinor-11-deoxy-PGF$_2$α, a compound according to claim 18.

20. A compound according to claim 17, wherein $R_5$ is hydrogen.

21. 2-Decarboxy-2-hydroxymethyl-2,2-difluoro-17-phenyl-18,19,20-trinor-11-deoxy-PGF$_2$α, a compound according to claim 20.

22. A compound according to claim 2, wherein $Z_2$ is —(CH$_2$)$_3$—(CH$_2$)$_g$—CF$_2$—.

23. A compound according to claim 22, wherein g is one.

24. A compound according to claim 23, wherein at least one of $R_3$ and $R_4$ is fluoro.

25. A compound according to claim 24, wherein $R_3$ and $R_4$ are both fluoro.

26. A compound according to claim 25, wherein $R_5$ is methyl.

27. 2-Decarboxy-2-hydroxymethyl-2,2,16,16-tetrafluoro-15-methyl-17-phenyl-18,19,20-trinor-11-deoxy-PGF$_1$α, a compound according to claim 26.

28. A compound according to claim 25, wherein $R_5$ is hydrogen.

29. 2-Decarboxy-2-hydroxymethyl-2,2,16,16-tetrafluoro-17-phenyl-18,19,20-trinor-11-deoxy-PGF$_1$α, a compound according to claim 28.

30. A compound according to claim 23, wherein at least one of $R_3$ and $R_4$ is methyl.

31. A compound according to claim 30, wherein $R_3$ and $R_4$ are both methyl.

32. A compound according to claim 31, wherein $R_5$ is methyl.

33. 2-Decarboxy-2-hydroxymethyl-2,2-difluoro-15,16,16-trimethyl-17-phenyl-18,19,20-trinor-11-deoxy-PGF$_1$α, a compound according to claim 32.

34. A compound according to claim 31, wherein $R_5$ is hydrogen.

35. 2-Decarboxy-2-hydroxymethyl-2,2-difluoro-16,16-dimethyl-17-phenyl-18,19,20-trinor-11-deoxy-PGF$_1$α, a compound according to claim 34.

36. A compound according to claim 23, wherein $R_3$ and $R_4$ are both hydrogen.

37. A compound according to claim 36, wherein $R_5$ is methyl.

38. 2-Decarboxy-2-hydroxymethyl-2,2-difluoro-15-methyl-17-phenyl-18,19,20-trinor-11-deoxy-PGF$_1\alpha$, a compound according to claim 37.

39. A compound according to claim 36, wherein $R_5$ is hydrogen.

40. 2-Decarboxy-2-hydroxymethyl-2,2-difluoro-17-phenyl-18,19,20-trinor-11-deoxy-PGF$_1\alpha$, a compound according to claim 39.

41. A compound according to claim 2, wherein $Z_2$ is cis-CH$_2$—CH=CH—(CH$_2$)$_g$—CH$_2$—.

42. A compound according to claim 41, wherein g is one.

43. A compound according to claim 42, wherein at least one of $R_3$ and $R_4$ is fluoro.

44. A compound according to claim 43, wherein $R_3$ and $R_4$ are both fluoro.

45. A compound according to claim 44, wherein $R_5$ is methyl.

46. 2-Decarboxy-2-hydroxymethyl-cis-4,5-didehydro-15-methyl-16,16-difluoro-17-phenyl-18,19,20-trinor-11-deoxy-PGF$_1\alpha$, a compound according to claim 45.

47. A compound according to claim 44, wherein $R_5$ is hydrogen.

48. 2-Decarboxy-2-hydroxymethyl-cis-4,5-didehydro-16,16-difluoro-17-phenyl-18,19,20-trinor-11-deoxy-PGF$_1\alpha$, a compound according to claim 47.

49. A compound according to claim 42, wherein at least one of $R_3$ and $R_4$ is methyl.

50. A compound according to claim 49, wherein $R_3$ and $R_4$ are both methyl.

51. A compound according to claim 50, wherein $R_5$ is methyl.

52. 2-Decarboxy-2-hydroxymethyl-cis-4,5-didehydro-15,16,16-trimethyl-17-phenyl-18,19,20-trinor-11-deoxy-PGF$_1\alpha$, a compound according to claim 51.

53. A compound according to claim 50, wherein $R_5$ is hydrogen.

54. 2-Decarboxy-2-hydroxymethyl-cis-4,5-didehydro-16,16-dimethyl-17-phenyl-18,19,20-trinor-11-deoxy-PGF$_1\alpha$, a compound according to claim 53.

55. A compound according to claim 42, wherein $R_3$ and $R_4$ are both hydrogen.

56. A compound according to claim 55, wherein $R_5$ is methyl.

57. 2-Decarboxy-2-hydroxymethyl-cis-4,5-didehydro-15-methyl-17-phenyl-18,19,20-trinor-11-deoxy-PGF$_1\alpha$, a compound according to claim 56.

58. A compound according to claim 55, wherein $R_5$ is hydrogen.

59. 2-Decarboxy-2-hydroxymethyl-cis-4,5-didehydro-17-phenyl-18,19,20-trinor-11-deoxy-PGF$_1\alpha$, a compound according to claim 58.

* * * * *